United States Patent
Ducker

(10) Patent No.: US 10,813,799 B2
(45) Date of Patent: Oct. 27, 2020

(54) LAYERED ABSORBENT STRUCTURE WITH WICKING PERFORMANCE

(71) Applicant: EAM Corporation, Jesup, GA (US)

(72) Inventor: Paul M. Ducker, Brunswick, GA (US)

(73) Assignee: EAM CORPORATION, Jesup, GA (US)

( * ) Notice: Subject to any disclaimer, the term of this patent is extended or adjusted under 35 U.S.C. 154(b) by 1080 days.

(21) Appl. No.: 14/707,050

(22) Filed: May 8, 2015

(65) Prior Publication Data
US 2015/0320617 A1 Nov. 12, 2015

Related U.S. Application Data

(60) Provisional application No. 61/991,091, filed on May 9, 2014.

(51) Int. Cl.
*A61F 13/537* (2006.01)
*A61F 13/15* (2006.01)
(Continued)

(52) U.S. Cl.
CPC ...... *A61F 13/537* (2013.01); *A61F 13/15707* (2013.01); *A61F 13/534* (2013.01);
(Continued)

(58) Field of Classification Search
CPC ...... A61F 13/53; A61F 13/534; A61F 13/537; A61F 13/53743; A61F 13/539; A61F 2013/53721; A61F 2013/53739; A61F 2013/53908; A61F 2013/53925; A61F 2013/530481; A61F 2013/530547;
(Continued)

(56) References Cited

U.S. PATENT DOCUMENTS 4,100,324 A * 7/1978 Anderson ............ C11D 17/049
156/167
4,443,512 A * 4/1984 Delvaux ............... A61F 13/533
428/162

(Continued)

FOREIGN PATENT DOCUMENTS

EP 0438113 7/1991
WO 2015171972 11/2015

OTHER PUBLICATIONS

Ducker, Paul M.; International Search Report and Written Opinion for PCT Application No. PCT/US2015/029807, filed May 8, 2015, dated Aug. 5, 2015, 8 pgs.

*Primary Examiner* — Laura C Powers
*Assistant Examiner* — Larissa Rowe Emrich
(74) *Attorney, Agent, or Firm* — Norton Rose Fulbright US LLP

(57) ABSTRACT

The present invention relates to a layered absorbent structure in the form of a laminate including liquid storage layers comprising particulate superabsorbent material and adhesive fibers. Notably, the absorbent structure includes a wicking layer positioned between the liquid storage layers, with the wicking layer desirably acting to improve fluid spreading and rewet performance of the absorbent structure. The wicking layer preferably comprises airlaid cellulosic fibrous material such as wood pulp, and may optionally include superabsorbent polymer. A bonding pattern of the wicking layer is oriented to enhance wicking and rewet performance.

18 Claims, 2 Drawing Sheets

(51) Int. Cl.
*B32B 5/08* (2006.01)
*A61F 13/534* (2006.01)
*B32B 5/02* (2006.01)
*B32B 7/12* (2006.01)
*B32B 5/26* (2006.01)
*A61F 13/53* (2006.01)
*A61F 13/539* (2006.01)

(52) U.S. Cl.
CPC ............... *B32B 5/022* (2013.01); *B32B 5/08* (2013.01); *B32B 5/26* (2013.01); *B32B 7/12* (2013.01); *A61F 2013/5395* (2013.01); *A61F 2013/530343* (2013.01); *A61F 2013/53454* (2013.01); *A61F 2013/530481* (2013.01); *A61F 2013/53739* (2013.01); *A61F 2013/53925* (2013.01); *B32B 2250/03* (2013.01); *B32B 2262/0253* (2013.01); *B32B 2307/718* (2013.01); *B32B 2307/72* (2013.01); *B32B 2555/00* (2013.01); *Y10T 156/1023* (2015.01)

(58) Field of Classification Search
CPC ...... A61F 2013/53454; A61F 13/15203; A61F 2013/15487; A61F 2013/15536; A61F 13/533; B32B 5/022; B32B 5/08; B32B 5/26; B32B 7/12; B32B 7/14; B32B 2250/03; B32B 2250/40; B32B 2262/0253; B32B 2307/718; B32B 2307/72; B32B 2555/00; B32B 2555/02; B01J 2219/0063; Y10T 428/2481; Y10T 428/249924–249925; Y10T 442/659–673; Y10T 442/69; Y10T 442/695; B31F 1/07
USPC ....... 604/358, 365, 367, 368, 378, 379, 380, 604/384; 428/196, 292.1–292.4; 442/381–393, 409, 413
See application file for complete search history.

(56) References Cited

U.S. PATENT DOCUMENTS

| 5,462,538 | A  | * | 10/1995 | Korpman    | A61F 13/51113 604/372 |
|-----------|----|---|---------|------------|-----------------------|
| 5,562,645 | A  | * | 10/1996 | Tanzer     | A61F 13/15203 604/358 |
| 5,593,399 | A  |   | 1/1997  | Tanzer et al. | |
| 6,675,702 | B1 |   | 1/2004  | Maksimow   | |
| 7,232,300 | B2 |   | 6/2007  | Walter et al. | |
| 2003/0135178 | A1 | * | 7/2003 | Hansen    | A61F 13/535 604/368 |
| 2004/0015142 | A1 |   | 1/2004 | Johnston et al. | |
| 2004/0236294 | A1 | * | 11/2004 | Drzewiecki | A61F 13/15203 604/366 |
| 2005/0118916 | A1 | * | 6/2005  | Ducker    | A61F 13/15203 442/385 |
| 2010/0137773 | A1 | * | 6/2010  | Gross     | A61F 13/53 602/43 |
| 2010/0318047 | A1 | * | 12/2010 | Ducker    | A61F 13/533 604/365 |
| 2012/0148821 | A1 | * | 6/2012  | Ducker    | A61F 13/5323 428/220 |

* cited by examiner

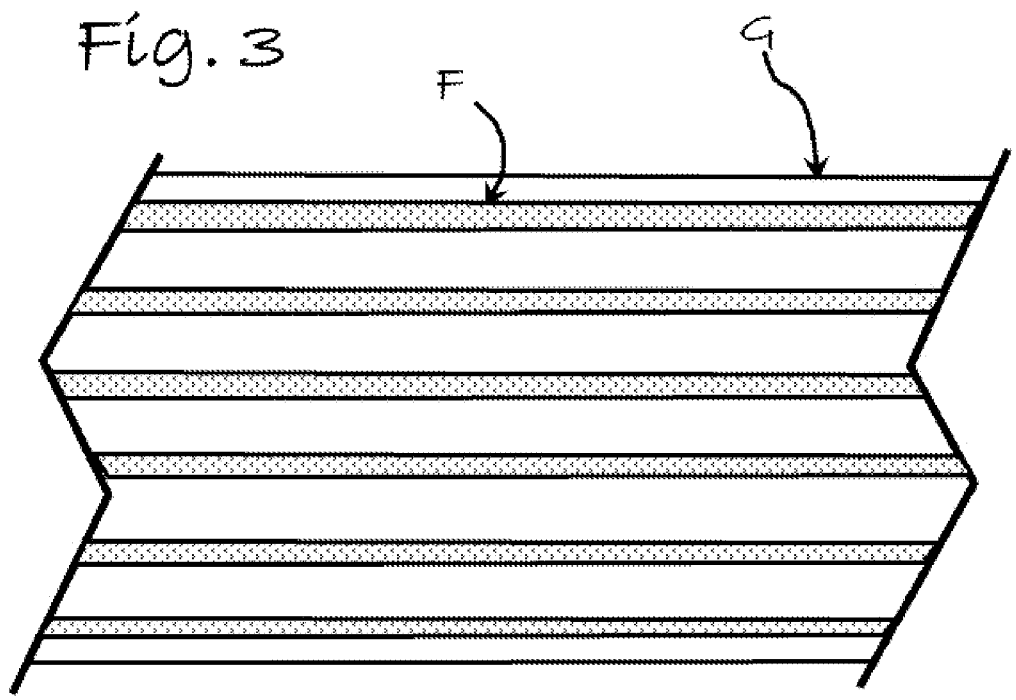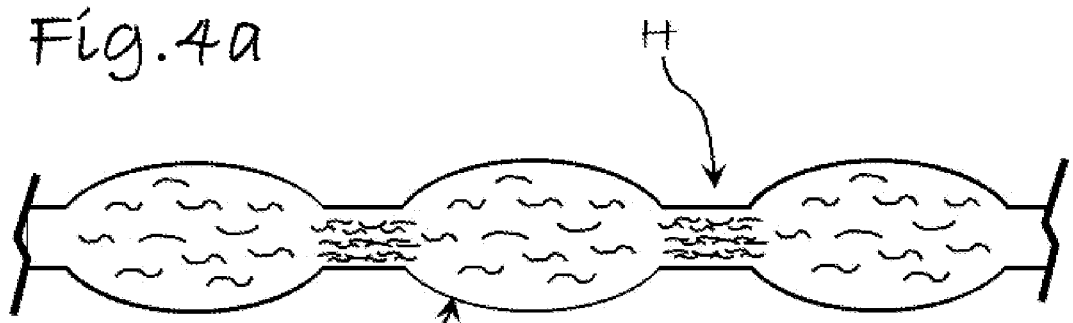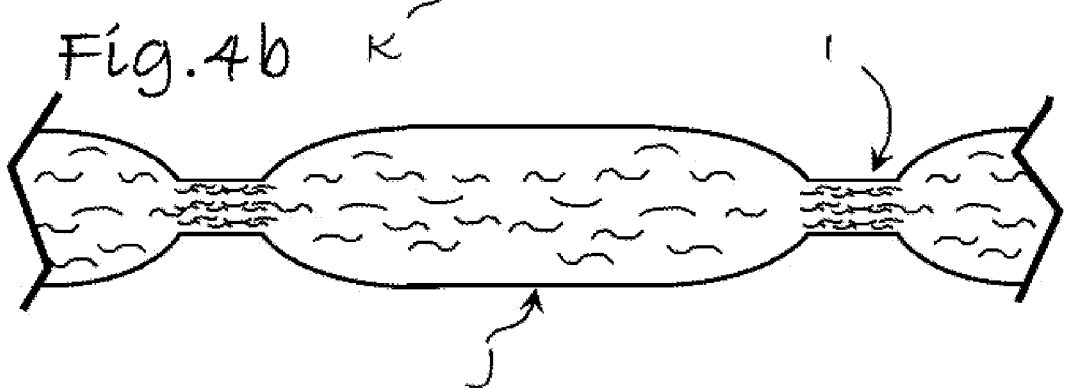

LAYERED ABSORBENT STRUCTURE WITH WICKING PERFORMANCE

FIELD OF INVENTION

The present invention relates generally to absorbent material for use in disposable absorbent articles, and more particularly to a layered absorbent structure including absorbent laminates that include particulate superabsorbent material and adhesive, with the absorbent structure including a wicking layer that improves fluid spreading and rewet performance.

DESCRIPTION OF THE RELATED ART

Absorbent cores in absorbent articles, such as disposable diapers, incontinence products, and feminine hygiene products, have become progressively thinner, with the amount of superabsorbent polymeric material (SAP) increasing, and the amount of wood pulp and other fibers generally decreasing.

Currently, certain product offerings comprise cores that include thin absorbent laminates. These laminates comprise upper and lower substrate layers, made of tissue for example, with an intermediate layer sandwiched between the upper and lower layers comprising particles of superabsorbent material and typically a thermoplastic adhesive composition to ensure the integrity of the laminate.

One such laminate is described in U.S. Patent Publication No. 2012/0148821, the disclosure of which is hereby incorporated by reference. A principal benefit of this type of laminate core is that it is extremely thin and flexible relative to its absorbent capacity. It has, however, been observed that this type of laminate does not spread or wick fluid in the longitudinal and transverse directions within the core to a satisfactory degree, as a result causing reduced utilization of the core, and less than satisfactory drying of the target area of the core as indicated by so-called rewet performance.

It has been found that in this type of laminate, merely replacing one of the substrate layers with a wicking layer, has not been satisfactory. First, the material becomes "sided" in the sense that the sequence of constituent layers differs from one face to the other. As a consequence, it can be necessary to flip over or invert the laminate as it is taken from a long running package such as a festoon box, in order to keep the correct side facing up, after it has inadvertently flipped over, which is typically complex to manage and not acceptable for commercial processing. Second, the most effective wicking layers typically attract liquid in order to cause it to wick and as a result tend to want to retain it after wetting and therefore present that retained wetness to the inner, liner side of the core formed from the laminate, where the liquid negatively affects the dryness of the product. Third, the transfer of liquid from the wicking layer to the adjacent SAP appears to be inefficient, so that at the periphery of the wetted area where the wicking layer is only damp, liquid is not well-transferred to the adjacent dry SAP. The wicking layer is thought to be most effective at drying the target location where liquid has entered the core when the liquid it has wicked away from that location in the x and y directions is transferred to the adjacent storage structures creating capillary suction within the wicking layer and drying action at the target location. Any effect which would improve this transfer of fluid from the wicking layer to the adjacent SAP in the storage structures would be advantageous to the action of the wicking layer.

The system of the present invention addresses these shortcomings by providing a thin, flexible absorbent core laminate with high absorbency that is not sided, and which significantly improves drying the target area of the core by more efficiently transferring liquid to the SAP at locations away from the point of insult, both external to and optionally within the wicking layer, wherein the structure maintains its integrity to a sufficient degree as to permit such performance even when subjected to repeated insults.

SUMMARY OF THE INVENTION

In one aspect of the present invention, there is provided an absorbent laminate that includes three substrates; an upper substrate, a lower substrate, a central wicking substrate situated between the upper and lower substrates. The laminate, includes two liquid storage layers, each comprising a mixture of superabsorbent polymer (SAP) and hot melt adhesive fibers, respectively disposed between adjacent ones of the aforementioned substrate layers, on respective opposite sides of the central wicking layer. In a second aspect of the present invention, the upper and lower substrates are tissue. In a third aspect of the present invention, the wicking substrate (also referred to hereinafter as the wicking layer) is comprised of hydrogen bonded airlaid material. In a fourth aspect of the present invention, the hydrogen bonded airlaid material is comprised of cellulosic fibers, tissue, and optionally up to 20% SAP. In a fifth aspect of the present invention, the hydrogen bonded airlaid material is bonded internally using an embossed bonding pattern, resulting in robustly bonded areas and other areas that are not bonded and allowed to assume a lower density than the bonded areas more suitable to efficient wicking. In a sixth aspect of the present invention, the bonding pattern of the wicking layer is situated such that in the structure is kept in tension in the thickness direction, stabilizing the density, as indicated by a density in the range of 0.08 g/cc to 0.25 g/cc. Optionally, the structure includes an oriented bonding pattern whereby fluid is free to travel in the longitudinal direction without having to transverse boundaries between bonded and unbonded regions, and while liquid traveling in the transverse direction must cross multiple boundaries between bonded and unbonded regions resulting in suppressed wicking in the transverse direction compared to wicking in the longitudinal direction.

The material of the present invention exhibits a Vertical Delamination Strength of at least 4N, has a centrifuge retention value of at least 18 g/g, and has a caliper of 3 mm or less.

In the preferred embodiment, the upper and lower substrates are comprised of tissue. The basis weight range for the tissue may be up to 40 grams per square meter (gsm), with a more preferred basis weight range of 10 gsm-25 gsm, with an even more preferred basis weight range from 15 gsm-20 gsm.

The SAP can be any type suitable for use in the absorbent articles in which the cores of the present invention are intended for use. Surface cross-linked SAP types are more generally preferred for their improved permeability. The basis weight of the SAP for each of the two liquid storage layers can range from 50 gsm to 500 gsm, with a more preferred basis weight range of 75-300 gsm, with an even more preferred basis weight range 100-200 gsm. The amount and type of SAP can differ between the two layers, but it is preferable that they be the same so if the material is flipped over, the performance is similar (ie, the laminate is not "sided".)

The adhesive is a hot melt adhesive, preferably a synthetic rubber based pressure sensitive type, with an add-on level in the range of 2%-15% of the SAP weight. A more preferable add-on range is 3%-9% of the SAP weight, depending on the glue type and the desired level of integrity.

The hydrogen bonded airlaid wicking layer of the present invention is comprised of cellulosic fibers, but optionally can contain SAP material. The cellulosic fibers can be any type, but preferably are paper pulp and even more preferably Kraft southern pine. The preferred range of the SAP content in the wicking layer is 0%-20%. The overall basis weight of the wicking layer is preferably in the range of 50 gsm-300 gsm, and is more preferably 75 gsm-200 gsm, and even more preferably 100 gsm-150 gsm. Bonding patterns for the wicking layer are preferably repeating land/sea patterns of bonded and unbonded areas, with bond dimensions yielding apparent density in the range of 0.08 g/cc-0.25 g/cc, and more preferably in the range of 0.10 g-cc-0.20 g/cc, dependent on the interaction of the bond pattern with the basis weight of the material. A preferred bonding pattern is of a type that suppresses wicking in the transverse direction by causing fluid wicking in that direction to cross multiple boundaries of bonded to unbonded areas.

The hydrogen bonded wicking layer preferably has a substrate on both faces, with each of the substrates preferably tissue, in order to contain any loose fibers in the unbonded regions.

Thus, the present invention comprises an absorbent laminate including a central wicking layer, and first and second liquid storage layers positioned in liquid-transferring relationship on respective opposite sides of said central wicking layer. The central wicking layer comprising hydrogen-bonded cellulosic fibrous material, with each of the first and second liquid storage layers comprising a matrix of adhesive filaments and absorbent particles, with the adhesive filaments adhering the first and second storage layers to respective opposite sides of the central wicking layer.

Each of the first and second liquid storage layers preferably comprises a cellulosic fiber tissue layer adhered to the respective matrix of adhesive filaments and absorbent particles on the side of the respective matrix opposite said central wicking layer. The central wicking layer is comprised of a hydrogen-bonded, airlaid cellulosic fibrous material bonded by applying heat and pressure. The central wicking layer preferably exhibits a Vertical Delamination Strength greater than 4N, and is preferably formed by a heated calender roll with an embossing pattern that does not bond the entire surface. This allows the wicking layer to be bonded in a fashion that yields the desired vertical delamination strength, which requires a undesirably high density, and leave unbonded areas at lower densities which will allow for faster wicking.

In the preferred form, the first and second liquid storage layers are of substantially equal basis weight, and the central wicking layer comprises a central portion formed from hydrogen-bonded wood pulp fibers, and first and second tissue layers hydrogen-bonded to respective opposite sides of said central portion. The central wicking layer may be substantially devoid of superabsorbent polymer, or may optionally contain SAP up to 20% by weight.

In practice, the present absorbent structure exhibits a Vertical Delamination Strength of greater than 4N.

Other objects, features, and advantages of the present invention will become apparent from the following detailed description.

BRIEF DESCRIPTION OF THE DRAWINGS

FIG. 3 is an illustration of a bonding pattern, open in one dimension, wherein bonded areas F comprise parallel lines separating unbonded areas G; and FIGS. 4a and 4b are illustrations of section views of a two different bonding patterns, wherein pattern H, FIG. 4a, has the entire structure under tension, while pattern I, FIG. 4b, has regions J that are relaxed, while K is held under tension by the bond H.

DETAILED DESCRIPTION OF THE INVENTION

Figure 1:
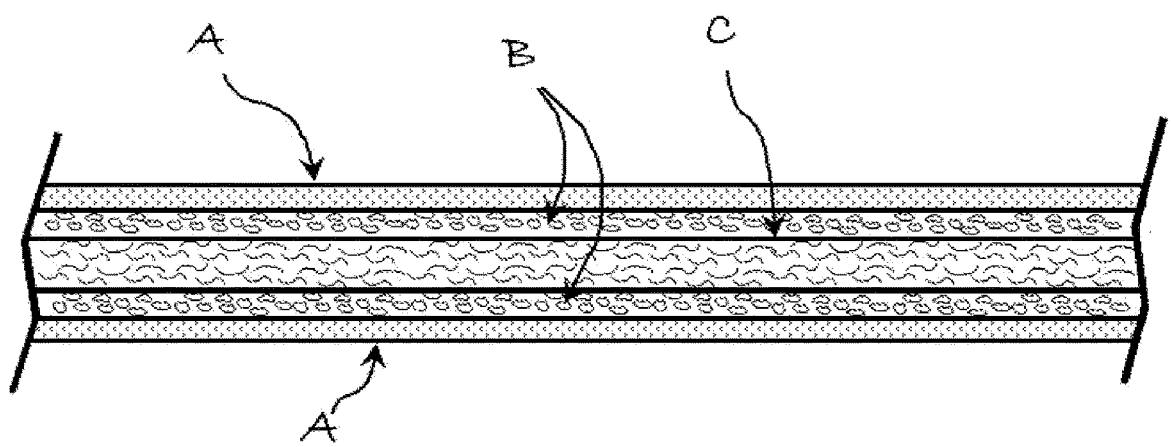
FIG. 1 is a section diagram of the laminate of the present invention, wherein upper and lower substrates A enclose adjacent layers of SAP and adhesive fibers B, with wicking layer C sandwiched between adjacent layers of SAP and adhesive fibers.
Figure 2:
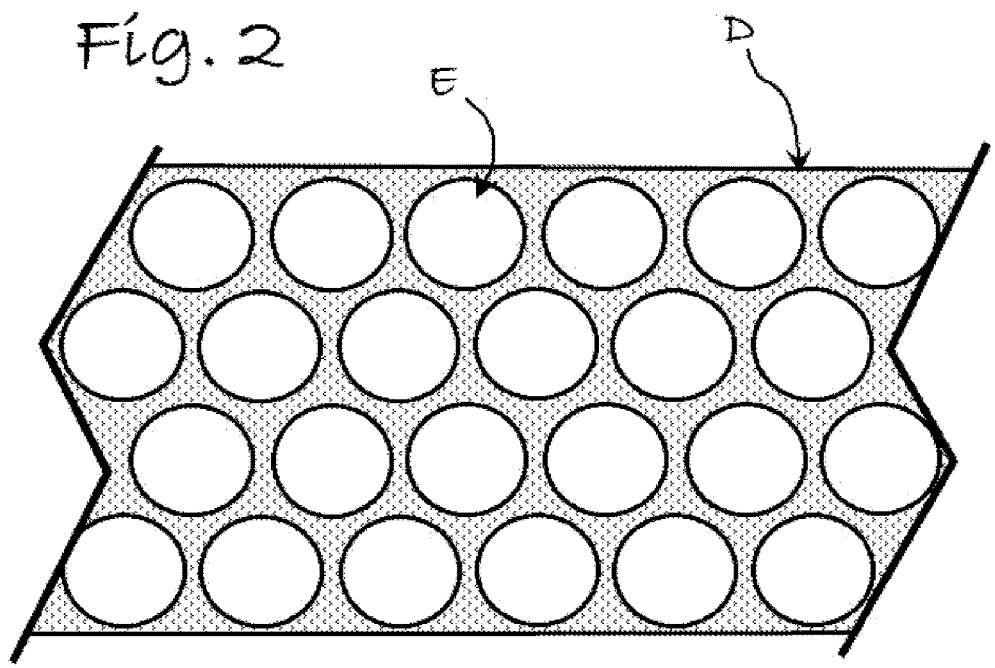
FIG. 2 is an diagrammatic illustration of a closed bonding pattern, wherein bonded areas D surround unbonded areas E.

While the present invention is susceptible of embodiment in various forms, there is shown in the drawings, and will hereinafter be described, presently preferred embodiments, with the that the present disclosure is to be considered as an exemplification of the invention, and is not intended to limit the invention to the specific embodiments illustrated.

The laminate of the present invention is comprised of three substrates, a lower and an upper substrate, and a central wicking layer between them. The lower and upper substrates can be comprised of any porous sheet material such as nonwoven fabrics, with exemplary materials being spun-bond, spunlace, or through-air bonded or the like, but are most preferably comprised of tissue. The basis weight range for the tissue may be up to 40 grams per square meter (gsm), with a more preferred basis weight range of 10 gsm-25 gsm, with an even more preferred basis weight range from 15 gsm-20 gsm. A suitable tissue grade is 17 gsm 3995 grade from Dunn Paper of East Hartford, Conn.

The present absorbent laminate further includes, two liquid storage layers each comprising a mixture of superabsorbent polymer (SAP) and hot melt adhesive fibers, respectively disposed between adjacent ones of the aforementioned substrate layers, on respective opposite sides of the central wicking layer. The superabsorbent material can comprise a variety of materials, including organic compounds, such as cross-linked polymers. "Cross-linked" is a commonly understood term and refers to any process for effectively rendering normally water-soluble materials substantially water insoluble, but swellable. Such polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. Organic high-absorbency materials can include natural materials, such as agar, pectin, and guar gum. In addition to organic materials, superabsorbent materials may also include inorganic materials, such as absorbent clays and silica gels. Preferred superabsorbent materials are crosslinked partially neutralized polyacrylates widely commercially used in disposable absorbent articles. The preferred embodiment would use a type that would be typical for the intended end use, and in the case of absorbent articles for urine applications, typically would be of the type that is surface crosslinked, in order to improve the permeability, while preserving the absorbent capacity. Examples include W125 SAP from Nippon Shokubai, N.A.I.I., Houston, Tex., and T9030 from BASF.

The superabsorbent material typically is in particle form and can be of any desired configuration, such as granulated powders, fibers, agglomerated spheres, and other shapes known to those skilled in the art. The particle size of the superabsorbent material may vary, but typically falls between about 20 microns to about 1000 microns.

The basis weight of the SAP for each of the two liquid storage layers can range from 50 gsm to 500 gsm, with a more preferred basis weight range of 75-300 gsm, with an even more preferred basis weight range 100-200 gsm. The liquid storage layers can contain differing amounts and types of SAP, but in a more preferred embodiment, each layer contains the same quantity and type in order to make the core material as symmetrical as possible from top to bottom.

The practical advantage to having a symmetrical absorbent core is that in high-speed converting applications for manufacture of disposable absorbent articles for which the laminate core of the present invention is particularly suited for use, long-running packages of the laminate, such as festoon boxes or spooled rolls, are typically preferred. While technologies exist to keep a particular side of the core taken from a festoon box facing upwards, such technologies are complicated. It is much simpler and more efficient to employ a core which is not "sided", that is, the side of the core that faces upwards doesn't matter, so if the web happens to flip over as it comes out of the package, it has no effect on product performance. The production process for applying the SAP/adhesive fiber layer has discreet limits to the performance of a single process step, and as such, the process is best run at the maximum value. Presuming each SAP storage layer is applied by similar equipment, throughput is maximized by making them at the same maximum basis weight so each is produced at the maximum speed for that basis weight.

The SAP-containing liquid storage layers of the laminate of the present invention also include fibers comprised of a thermoplastic adhesive composition. The thermoplastic adhesive composition is preferably of a type that is suitable for use in the production of disposable hygiene articles and is preferably formulated such that it is tacky at room temperature. According to the invention, the thermoplastic adhesive composition is a thermoplastic, hot-melt adhesive composition. A thermoplastic, hot-melt adhesive composition generally comprises one or more polymers that provide cohesive strength, and a tackifying resin or similar material that provides adhesive strength, and optionally may include waxes, plasticizers or other materials that modify viscosity, as well as other additives, such as antioxidants and stabilizers.

According to more preferred embodiments of the present invention, the thermoplastic adhesive composition comprises a pressure-sensitive, thermoplastic adhesive composition, more preferably, a synthetic rubber-based pressure sensitive adhesive. In specific embodiments, the thermoplastic adhesive composition may be a styrene-butadiene-styrene block copolymer (SBS) or a styrene-isoprene-styrene (SIS) hot melt thermoplastic adhesive composition. An example of a preferred thermoplastic adhesive composition is SP507 adhesive from Savare Specialty Adhesives of Milan, Italy, which has shown thermal stability in the viscosity ranges listed below. Another example of a preferred thermoplastic adhesive composition is E60W adhesive also from Savare Specialty Adhesives. The amount of thermoplastic adhesive composition applied should be kept generally at the minimum amount necessary to provide a laminate with acceptable integrity.

The adhesive is preferably a type made with ingredients that are suitable for use in the end use product, with an add-on level in the range of 2%-15% of the SAP weight. A more preferable add-on range is 3%-9% of the SAP weight, depending on the glue type and the desired level of structural integrity.

The wicking layer is a hydrogen bonded, airlaid material, such as generally described in U.S. Pat. No. 5,866,242, the disclosure of which is hereby incorporated by reference. In accordance with the preferred embodiment, the material is made using air-laying means well known in the art. Cellulosic fibers (e.g., wood pulp) are processed using a hammer mill to individualize the fibers. The individualized fibers are optionally blended with SAP particles and pneumatically conveyed into a series of forming heads. The distribution of absorbent materials can be controlled separately for each forming head. Controlled air circulation or mechanical agitators in each chamber produce a uniform distribution, and the fibers are deposited via a vacuum onto a moving web of porous carrier substrate (e.g., tissue) thus forming a uniform moving web of fibers. The moving web is subsequently compressed and an additional substrate (e.g., tissue) is added to the upper surface to enclose the loose fibers. The web is then hydrogen bonded using a heated calendar roll, with a bonding pattern engraved into the surface to form hydrogen bonds in the compressed regions. The resulting web is formed into rolls for subsequent handling. The heat and pressure applied interact with the moisture contained in the cellulosic fibers to produce bonds that are at least minimally stable after wetting, as necessary to maintain bonding under external, in-use mechanical forces, and to resist the debonding forces generated by the swelling of the hydrating SAP. Those skilled in the art can balance material basis weight and line speed with the levels of heat and pressure required to result in the proper bonding given the particular bonding pattern. Without the addition of heat, extreme pressure is otherwise required to form the desired degree of liquid stability in bonds within the wicking layer.

A significant factor governing the degree of bonding is the percent of bonded area in the embossed bonding pattern, such as a land—sea type pattern. For the purposes of the wicking layer material of the present invention, the percent bond area is desirably in the range of 5% to 50% of the surface, with more preferably in the range of 10% to 40%, and even more preferably in the range of 15%-30%. The minimum dimension of the unbonded area generally interacts with the basis weight to determine the density. While precise predictive analysis is complex, Those skilled in the art can derive the necessary dimensions for a particular pattern to yield the desired density either mathematically or by trial and error. To avoid large scale variation in the material properties, the bond pattern should be repeating. An exemplary bonding arrangement is a bond pattern of parallel lines on 3.9 mm centers, with a bonded surface each 1 mm wide. Bond pattern dimensions of the wicking layer of the present invention yield apparent density in the range of 0.08 g/cc-0.25 g/cc, and more preferably in the range of 0.10 g-cc-0.20 g/cc, with apparent density dependent on the interaction of the bond pattern with the basis weight of the material. A preferred bonding pattern is of a type that suppresses wicking in the transverse direction by causing liquid wicking in the transverse direction to repeatedly cross from between bonded and unbonded regions.

Cellulosic fibers that can be used in a wicking layer of the present invention are well known in the art and include wood pulp, cotton, and flax fibers, peat moss, as well as regenerated cellulose such as viscose rayon. While less wettable synthetic fibers such as thermoplastic fibers can be included using the airlaid process, these are undesirable for the purposes of the wicking layer of the present invention because they reduce the wettability of some of the pores in the wicking layer, and as a result reduce the wicking properties of the resultant material. Wood pulp is most preferred. Pulps can be obtained from mechanical or chemimechanical processes, sulfite, kraft, pulping reject materials, organic solvent pulps, etc. Both softwood or hardwood species are useful, although softwood pulps are preferred, with the most preferred being Kraft southern pine. An example of a suitable pulp is J-LDE grade pulp commercially available from Rayonier in Jesup, Ga.

Suitable carrier substrates for the hydrogen bonded airlaying process can include nonwovens that form bonding to the cellulose fibers under heat and pressure. These include chemical bonded nonwovens, through-air bonded nonwovens that use certain types of bicomponent binder fibers, or spunlaced nonwovens that contain a suitable amount of regenerated cellulose fibers to form useful hydrogen bonds. The preferred substrate, however, is tissue, with the most suitable being a porous type such as 3995 grade from Dunn Paper of East Hartford, Conn.

The absorbent laminate according to the present invention may be manufactured according to processes described in US Patent Publication No. 2012/0148821. According to one such process, a roll or sheet of laminate can be made by metering a free-falling curtain of SAP particles and mixing the curtain of SAP particles with hot melt thermoplastic adhesive composition fibers. The curtain of hot melt adhesive fibers can be generated by any of the commercially available hot melt equipment such using the UFD applicator head and the standard Omega 5,5 nozzles from ITW Dynatec in Hendersonville, Tenn.

The resulting mixture is then directed onto a moving substrate (lower substrate). The wicking layer is directed on top of the SAP-adhesive mixture to form a sandwich structure. The adhesive properties of the hot melt bonds this assembly together. A second mixture of SAP and hot melt adhesive fibers is generated in a similar fashion as the first and is deposited on the wicking layer side of the moving laminate sheet. Finally, the upper substrate is fed as a moving sheet, and is combined with this second layer of SAP and adhesive fiber mixture to form the final structure of the present invention. The laminate may then be rolled up and/or cut into segments sized for use in an absorbent article. Methods and apparatuses for metering SAP and mixing the SAP with the hot melt thermoplastic adhesive composition are available commercially and known to those skilled in the art.

The wicking layer is produced using established airlaying technology. Equipment for producing airlaid nonwovens is commercially available such as that offered by Dan Web of Aarhus, Denmark. To produce the wicking layer, a carrier layer of tissue is first fed onto a moving wire screen and the fluff pulp and optional SAP mixture is then deposited on this wire screen using air laying methods well known to those skilled in the art. In this type of equipment, the fluff pulp is fed in the form of sheets into hammermills which defiberize the pulp into individualized fibers and suspend it in an airstream directing it through ducts to the forming heads on the airlaid line. SAP is provided in supersacks and is fed directly to metering devices in the forming heads. A second continuous moving layer of tissue is combined on top of the moving web, sandwiching the pulp (and optional SAP material) between two layers of tissue in order to contain any loose fibers in the unbonded portions of the web.

This assembly is then compacted between steel rolls, and then is directed into the bonding calender. The land-sea bonding patterns can be formed in many different ways, but one way is to have an engraved calender on the top that carries the bonding pattern mated to a generally smooth calender on the bottom. The calenders are heated and loaded to sufficient pressure to produce the desired level of hydrogen bonding in the moving web. Sufficient bonding is preferably provided to allow for the at least 4N vertical delamination strength required for any substrate in the laminate, but excessive bonding will undesirably result in cut fibers and poor wicking Appropriate process conditions are dependent on the web and the line speed, and can be set up by those skilled in the art. The resulting hydrogen bonded airlaid is then provided to the lamination process described above, either directly as a moving web or in the form of a roll to be fed to the process.

One of the desirable aspects of this laminate type is the thinness of the resultant core. The cores of the present invention are very thin. Samples of exemplary materials were measured for caliper. These values are in table 1 below:

TABLE 1

| Caliper measurements | Caliper (mm) | |
|---|---|---|
| | AVERAGE | s |
| Example 1 material | 2.1 | 0.014 |
| Example 2 material | 2.9 | 0.07 |
| Example 3 material | 1.8 | 0.14 |

The material of the present invention has a caliper 3 mm or less.

The vertical delamination strength needs to be sufficiently great in order to allow the core of the present invention to be handled in a typical converting operation. Samples of the example materials were measured for Vertical Delamination. These values are reported in table 2 below:

TABLE 2

| Vertical Delamination measurements | Delamination (N) | |
|---|---|---|
| | AVERAGE | s |
| Example 1 material | 4.4 | 1.9 |
| Example 2 material | 5.1 | 0.96 |
| Example 3 material | 5.6 | 0.25 |

An experiment was devised to illustrate the effectiveness of the configuration of the material of the present invention to most effectively reduce the wetness of the point where the fluid entered the core material as indicated by rewet results. In order to conveniently construct the various configurations for testing, the layers comprising the core of the present invention were produced discreetly so that they could be stacked upon one another in different fashions to represent the structure of the core of the current invention as well as to represent the less effective alternative configurations. Finally, cores of the present invention were compared to these stacked mock-ups to show similar results suggesting that the mock-up were valid representations. The following discreet materials were produced to approximate the different layers in the material of the present invention:

The following are materials used:
1. C210: This is a mixture of SAP and hot melt glue fibers laminated between two layers of tissue. The tissue is 17 gsm 3995 grade from Dunn Paper. The SAP is 171 gsm T9030 from BASF. The hot melt adhesive is 5 gsm SP507 from Savare. This represents each of the storage layers in the material of the present invention
2. J090: this is a hydrogen bonded airlaid material, comprised of 2 plies of 17 gsm 3008 tissue from Clearwater Paper, with 56 gsm Rayonier Rayfloc J-LDE fluff pulp airlaid between them. The material is hydrogen bonded between two calendar rolls heated to 170 C with a corduroy embossing pattern with 1 mm wide parallel embossing lines separated by 2.9 mm of unbonded width. Sufficient pressure is applied to make a destructive bond with the tissue, but not split the material. This represents the wicking layer in the material of the present invention.
3. C400: This is a mixture of SAP and hot melt glue fibers, laminated between two layers of tissue. The tissue is 17 gsm 3995 grade from Dunn paper. The SAP is 351 gsm T9030 from BASF. The hot melt adhesive is 15 gsm SP507 from Savare. This represents an equivalent of two storage layers in a control for the material of the present invention that does not have a wicking layer. The monolithic structure is thought to be a better representation than two pieces of C210 stacked upon one another.
4. Coverstock: 20 gsm spunbond polypropylene.

The ultimate purpose for providing the wicking layer is to improve the drying of the target area where fluid is added to the core, as indicated by rewet test results. An experiment was conducted using mock-ups to show the improvement in drying by adding a wicking layer in a sandwich structure (compared to a control without a wicking layer), to show the superiority of having the wicking layer sandwiched rather than on top, and to show that the material of example 1 performs in a similar manner as the "sandwich" structure mock up in the experiment, suggesting the mock-ups are accurate representations for this result.

Experiment 1
Mock-Up for Experiment 1
'n=3-each 100 mm×300 mm cores were cut from the materials above and were stacked on top of the other in the following configurations.
Variant 1—Wicking Layer on top: Two layers of C210 on the bottom with J090 on top, with coverstock on top of that.
Variant 2—Sandwich: Two layers of C210 with J090 sandwiched between, with coverstock on top. This represents the material of the present invention.
Variant 3: No wicking layer C400 with coverstock on top. This represents a control with no wicking layer.
Variant 4: Material from Example 1. This provides an indication of the accuracy of how well variant 2 represents the actual material of the present invention.

Rewet Test Procedure:
A fluid doser was used that has a 1-inch inside diameter vertical dosing tube that feeds through the center of a 4-inch square footpad that weighs 988 grams, which was placed on the center of each 100 mm×300 mm core mock-up. 100 ml of 0.9% Saline was added through the doser which then drained down into the core sample below. The doser was removed after the dosing and the sample was allowed to equilibrate for 30-minutes. After equilibration, stacks of ten (10) Ahlstrom No. 4×7 cm filter paper circles were assembled and preweighed. They were placed on the wet center of the sample and a 0.7 psi weight was placed on each stack. After 2-minutes exactly, the stack was removed and weighed. The tare weight of the filter papers was subtracted to yield the weight of liquid absorbed, which was recorded as the rewet in grams. The steps above were then repeated for a second insult, with the rewet being recorded as before.

TABLE 4

| Configuration | Test | Sample 1 | Sample 2 | Sample 3 | AVERAGE | S |
|---|---|---|---|---|---|---|
| Variant 1: Wicking Layer on Top | 1st Rewet | 0.05 | 0.05 | 0.04 | 0.05 | 0.01 |
| | 2nd Rewet | 1.56 | 4.39 | 1.16 | 2.37 | 1.8 |
| Variant 2: Sandwich | 1st Rewet | 0.04 | 0.05 | 0.04 | 0.04 | 0.01 |
| | 2nd Rewet | 0.02 | 0.01 | 0.08 | 0.04 | 0.04 |
| Variant 3: No Wicking Layer Control | 1st Rewet | 0.05 | 0.05 | 0.06 | 0.05 | 0.01 |
| | 2nd Rewet | 1.84 | 1.84 | 2.17 | 1.95 | 0.19 |
| Variant 4: Example 1 | 1st Rewet | 0.05 | 0.04 | 0.04 | 0.04 | 0.01 |
| | 2nd Rewet | 0.03 | 0.02 | 0.03 | 0.03 | 0.01 |

The first rewets were all 0.06 g or less. There is a sufficient amount of SAP directly beneath the wetted target to absorb the liquid effectively without having to rely on more spreading of the liquid than all of the variants were capable of. The Variant 2 Sandwich structure demonstrates significantly improved second rewet compared to the Variant 3 Control. It also demonstrated a directionally improved second rewet compared to having the wicking layer on the top. The variant 4 Example 1 material performed in a similar manner as the variant 1 mock-up and was not significantly different, suggesting the mock-up variant 2 is a valid representation.

While not wanting to be constrained by any particular theory, it is believed that adding the wicking layer on top of the assembly probably spreads liquid away from the wetted area, bringing some reduction in the fluid in the center of the core. However, the transfer of liquid to the dry SAP in the periphery of the wetted area is inefficient, and as a result the highly wettable wicking layer retains a great deal of fluid presenting a wet surface through the coverstock to the filter paper stack in the rewet test. In contrast, in the sandwich structure, it is believed that with two faces interfacing with the SAP, the wicking layer transfers more fluid to the SAP at locations away from the target where liquid enters the core, transporting more fluid away from the target and more effectively drying the wet center. In addition, it is sandwiched below a layer of SAP laminate and as such it is believed any wetness in that layer is not presented directly through the coverstock to the filter papers in the rewet test.

Vertical Delamination Procedure
Vertical Delamination Procedure. First, a tensile tester (Zwick Z005 Tensile tester) is set up to cause compression between two parallel platens at least 2-inches in diameter. Next, a 2-inch circular sample of the inventive laminate is prepared and attached to the upper platen. In particular, a double coated tape, such as Spectape type ST 550, is used to attach the sample to the upper platen. The bottom platen is covered with a piece of 3M double coated foam tape, or equivalent, with the release strip removed, making the surface of the lower platen adhesive with a slightly compliant surface to bond well with the irregular surface of the laminate. Subsequently, the Zwick Z005 Tensile tester was cycled as follows: the upper platen was moved toward the lower platen until the sample was compressed with a force of 35 N. The sample then became attached to both the upper and lower platens. After this force level is achieved, the upper platen was moved away from the lower platen at a rate of 75 mm/min. During the separation of the platens, the sample was delaminated. The maximum force value during this tensile mode corresponds to the extent of bonding. These delamination forces were recorded (expressed in Newtons.)

Caliper Procedure:

Caliper is measured using an Emveco Microgauge Model 200A set to measure the sample under a 0.0725 psi foot pressure. A 200 mm×300 mm hand sheet sample of the material is cut and tested in 6 places. The average function of the Emveco is activated and this value is recorded.

Wicking Layer for Example 1:

A continuous moving sheet of 17 gsm 3008 tissue available from Dunn Paper in East Hartford, Conn. is provided as a carrier sheet on a Dan Web airlaid line. Lighthouse grade fluff pulp from Domtar in Plymouth, N.C. is defiberized and fed mixed with a small amount of SA65s SAP from Sumitomo in Singapore. A sheet of 17 gsm 3995 tissue from Dunn Paper in East Hartford, Conn. is combined as a top layer to the core. The web had a basis weight average of 105 gsm and contained approximately 5% SAP. This web is fed into a calender with an upper roll that has a bonding pattern of parallel bonded lines approximately 1 mm wide with approximately 2.9 mm of unbonded space between them, running in the machine direction. The lower roll that mates to it has a linen pattern, similar to that of a linen sheet. A roll temperature of 175 C was used and enough pressure was applied to result in a vertical delamination values of between 5 and 10 N. This material was wound on a roll and provided to the lamination process.

Example 1

A curtain of E60W hot melt adhesive fibers from Savare in Milan Italy was provided by a UFD hot melt spray applicator head using Omega 5.5 nozzles from ITW Dynatec in Hendersonville, Tenn., and mixed with a continuous curtain of T9030 SAP from BASF, with this mixture deposited onto a moving sheet of 17 gsm 3995 tissue available from Dunn Paper in East Hartford, Conn. at an add-on rate of 5.3 gsm adhesive and half of the SAP. The wicking layer for Example 1 above was then fed as a moving web and combined on top of this mixture of SAP and glue to form a sandwich. A second similar layer of 5.3 gsm hot melt adhesive fibers and the second half of the SAP were generated and deposited in a similar manner as the first on top of the wicking layer. Finally a second moving web of 3995 tissue was combined on top of the second layer of SAP and hot melt adhesive fibers. The SAP add-on was sufficient to yield a material with an average basis weight of 489 gsm.

Wicking Layer for Example 2:

The wicking layer for example 2 was formed in the same manner using the same equipment, configurations, and materials as the wicking layer for example 1. The only difference is that the pulp and SAP were fed in different proportions to yield a material of approximately 300 gsm in basis weight containing 5% SAP dispersed rather than 100 gsm in basis weight with 5% SAP dispersed.

Example 2

The material for example 2 was made in a manner similar to example 1, except the wicking layer for example 2 was used and the SAP flow, which was evenly divided between the two layers, was sufficient to yield a material with a basis weight average of 685 gsm.

Wicking Layer for Example 3:

The wicking layer for example 3 was similar to the wicking layer for example 1, with the exception that the pulp was fed at a rate where the overall basis weight of the material was around 100 gsm. The other difference was that instead of the parallel lines, the pattern used has parallel wavy lines that run in the longitudinal direction, have a spacing pitch of 4.2 mm, and a bonded line width of about 1 mm.

Example 3

The material for example 3 is similar to the material for example 1 with the exception that the wicking layer for example 3 was used, and the SAP was equally divided between the two layers to yield an overall basis weight that averaged 343 gsm.

It has been noticed that the transfer of liquid from the portions of the wicking layer near the periphery of the wetted area to the adjacent unwetted SAP does not appear to be very efficient. Without being bound to any particular theory, the SAP particles immediately in contact with the just damp wicking layer appear to partially swell. Liquid doesn't appear to transfer well to the grains behind those and the swelling of the adjacent granules seems to act as a separation. There is no fine capillary structure amongst the partially swelled SAP particles with which to efficiently transfer the dampness through the SAP. Without wanting to be bound by any particular theory, it is thought that by placing the wicking layer in the center of the material rather than on one face, twice as many SAP particles are in direct contact with the wicking layer, presumably doubling the intensity of any fluid transfer.

It is thought that hydrogen bonding patterns comprised of parallel bond lines tend to suppress liquid wicking in the transverse direction, resulting in a wetter material at the point of fluid insult than for a material with a bonding pattern that wicks in both directions without such suppression. It is thought that liquid does not tend to want to repeatedly traverse the boundaries between dense bonded and less dense unbonded regions as it moves transversely through the core. The liquid wicks a further distance in the unimpeded longitudinal direction, but the point of insult remains wetter yielding poorer rewets than materials without suppressed wicking. It would be thought then that a wicking layer with this type of bond pattern and greater wetness would not be desirable to produce the best rewets in the material of the present invention.

It was also supposed that a wicking layer containing SAP will be less efficient at transferring liquid to the adjacent SAP storage layers at locations away from the point of fluid insult into the core because the SAP within the wicking layer will absorb part of a fixed quantity of a liquid insult, making the wicking layer seem drier as well as reducing the wetness that causes the liquid to wick away from the point of insult. Additionally, it is supposed that having SAP swell within a wicking layer breaks the bonds within the layer, causing it to swell and the capillaries to become larger, which reduces the distance a given amount of fluid will wick away from the point of insult. The resulting smaller, drier wet spot should transfer less fluid to the SAP layers.

Contrary to the suppositions above, in the material of the present invention, it has been observed that wicking layers with parallel bonding patterns that suppress liquid wicking in the transverse direction and contain up to 20% SAP appear to do very well as wicking layers, producing the desired dryness at the point of liquid insult, enhancing rewet performance. The following experiment was devised to suggest why this might be.

To understand the effects it was necessary to devise a way to mock-up a representation of the system of the present invention that made it possible to directly measure the wetness in the center of the core, as well as directly measure the amount of liquid absorbed from the wicking layer into the adjacent SAP storage layers at specific locations away from the point of insult in both the longitudinal and transverse directions. For purposes of this experiment only, wetness will be defined as the grams of liquid per gram of material, In order to directly measure the wetness of the spot where liquid was insulted into the core, a 2-inch circular piece of circle embossed wicking layer with a low SAP content was placed on the core at the target point, so that liquid could be insulted into the core through it, and it could be simply removed and weighed after equilibration to indicate the wetness of the core below. In order to directly measure the liquid transferred from the wicking layer to the adjacent SAP layers at locations distant to the point of insult, the SAP layers were represented by 2-inch circles of SAP laminate, which were placed on the wicking layer at specific locations relative to the point of fluid insult. Liquid that wicked through the wicking layer below them would transfer into these 2-inch circles as it would the storage layers of the material of the present invention and then after equilibration, these pieces could be removed and weighed directly to indicate the amount of fluid transferred at the specific locations relative to the insult point. While the SAP storage layer circles do not cover the entire surface of the wicking layer sample, storage layer located in the transverse direction and in the longitudinal direction at 75 mm from the insult point is equally represented. Finally, by peeling the SAP laminate circles in half and placing one half on top and one half on the bottom, this represents the relative advantage of having the wicking layer sandwiched in between the two SAP layers.

Two wicking layer materials were selected for evaluation as wicking layers. Both were very close to 100 gsm. One was circle bonded, with unbonded circles roughly 5 mm in diameter on 6 mm centers, surrounded by bonded area. The second was "corduroy" bonded, with parallel bonded lines about 1 mm wide on 3.9 mm centers with unbonded areas in between. Both contain a small percentage of SAP, with the "corduroy" sample containing somewhat more SAP, with a centrifuge retention of 7.45 g/g vs a centrifuge retention of 5.25 g/g for the circle embossed material.

The following experiment was performed. A 200 mm×300 mm hand sheet of each type of wicking layer was placed flat. The center of each was marked, and a 2-inch circular piece of the "circle" wicking layer material was cut with a die and placed on the mark, as a device for measuring the retained wetness at the center of each sample wicking layer. This circular piece could be removed and weighed and due to its similarity in composition and basis weight to the wicking layer below, the wetness of the center of the hand sheets could be thus indicated. At 75 mm in the transverse direction and 75 mm in the longitudinal direction from the center mark, another pair of marks were put on the hand sheet. On each of these marks was placed a 2-inch circular piece of 800 gsm absorbent laminate, representing the SAP strata, i.e., the liquid storage layers of the present absorbent structure, in each direction. At this high basis weight, these laminate elements are capable of absorbing any amount of liquid presented to it by the wicking layer.

5 configurations were made:

Variant 1: "Circle", with no laminate pieces (as a control)

Variant 2, "Corduroy" with no laminate pieces (as a control)

Variant 3, "Circle", with two SAP laminate pieces

Variant 4: "Corduroy", with two SAP laminate pieces.

Variant 5: "Corduroy" with two SAP laminate pieces that have been split into two layers, with half placed on the back surface of the handsheet at each mark, and half placed on the front surface of the handsheet of each mark, to represent any advantage of the sandwich configuration absorbing from both sides rather than one side.

A 10 ml insult of 0.9% saline was slowly poured onto the center circle of "circles" material, which then wicked outwards through the wicking layer below it. When the wet spot reached the longitudinal and transversely placed circles of 800 gsm SAP laminate, liquid would be absorbed into the SAP laminate according to how wet the wicking layer was below it. After 15-minutes of equilibration, the "circle" wetness-measuring piece was removed and weighed to see how dry the center had become (the goal of having a wicking layer), the transversely and longitudinally located SAP laminate circles were removed and weighed to see how much liquid had been transferred to these pieces in each direction, and finally, the length and width dimensions of the wetted area.

| Configuration 1: "Circles" no SAP laminate pieces Control 1 Basis Wt: 96 gsm | | | | | | |
|---|---|---|---|---|---|---|
| | Wet Area | | Wetness of center removable piece | Liquid Absorbed in the SAP laminate removable pieces(g) | | |
| Condition: | Length (mm) | Width (mm) | Center (g/g) | Transverse (g) | Longitudinal (g) | Sum of both (g) |
| 1st 10 ml insult | 220 | 200 | 4.8 | N/A | N/A | N/A |
| 2nd 10 ml insult | 295 | 200 | 5.6 | N/A | N/A | N/A |
| 3rd 10 ml insult | 300 | 200 | 5.6 | N/A | N/A | N/A |

| Configuration 2: "Corduroy" no SAP laminate pieces control 2 Basis Wt 101 gsm | | | | | | |
|---|---|---|---|---|---|---|
| | Wet Area | | Wetness of center removable piece | Liquid Absorbed in SAP laminate removable pieces (g) | | |
| Condition: | Length (mm) | Width (mm) | Center (g/g) | Transverse (g) | Longitudinal (g) | Sum of both (g) |
| 1st 10 ml insult | 260 | 85 | 4.2 | N/A | N/A | N/A |
| 2nd 10 ml insult | 300 | 100 | 5.0 | N/A | N/A | N/A |
| 3rd 10 ml insult | 300 | 140 | 5.5 | N/A | N/A | N/A |

Configuration 3: "Circles" with SAP laminate pieces
Basis Wt 100 gsm

| Condition: | Wet Area Length (mm) | Wet Area Width (mm) | Wetness of center removable piece Center (g/g) | Liquid Absorbed in SAP laminate removable pieces (g) Trans-verse (g) | Liquid Absorbed in SAP laminate removable pieces (g) Longi-tudinal (g) | Liquid Absorbed in SAP laminate removable pieces (g) Sum of both (g) |
|---|---|---|---|---|---|---|
| 1st 10 ml insult | 225 | 200 | 4.2 | 0.3 | 0.3 | 0.6 |
| 2nd 10 ml insult | 290 | 200 | 5.2 | 1.0 | 0.7 | 1.7 |
| 3rd 10 ml insult | 300 | 200 | 5.4 | 2.6 | 1.7 | 4.3 |

Configuration 4: "Corduroy" with SAP laminate pieces
Basis Wt 100 gsm

| Condition: | Wet Area Length (mm) | Wet Area Width (mm) | Wetness of center removable piece Center (g/g) | Liquid Absorbed in SAP laminate removable pieces(g) Trans-verse (g) | Liquid Absorbed in SAP laminate removable pieces(g) Longi-tudinal (g) | Liquid Absorbed in SAP laminate removable pieces(g) Sum of both (g) |
|---|---|---|---|---|---|---|
| 1st 10 ml insult | 250 | 100 | 3.7 | 0.0 | 1.9 | 1.9 |
| 2nd 10 ml insult | 280 | 135 | 4.7 | 0.6 | 3.0 | 3.5 |
| 3rd 10 ml insult | 300 | 150 | 5.0 | 1.2 | 4.7 | 5.9 |

Configuration 5: "Corduroy" with laminate on both sides
Basis Wt 100 gsm

| Condition: | Wet Area Length (mm) | Wet Area Width (mm) | Wetness of center removeable piece Center (g/g) | Liquid Absorbed in SAP laminate removeable pieces(g) Trans-verse (g) | Liquid Absorbed in SAP laminate removeable pieces(g) Longi-tudinal (g) | Liquid Absorbed in SAP laminate removeable pieces(g) Sum of both (g) |
|---|---|---|---|---|---|---|
| 1st 10 ml insult | 235 | 90 | 3.2 | 0.3 | 2.1 | 2.4 |
| 2nd 10 ml insult | 270 | 135 | 4.4 | 0.3 | 3.6 | 3.9 |

Preliminary and confirming testing of configurations 3 and 4 for two insults yielded similar relative results between the two as seen above.

It was found in these results that when liquid was absorbed into the SAP laminate removable pieces, the removable piece in the center became less wet, suggesting the system in the above experiment is functioning in a similar manner as the material of the present invention.

To the degree that the mock-ups above represent the relative performance of the actual laminate of the present invention, these results unexpectedly point to using the Corduroy bonding pattern and including some additional SAP in that material as yielding both the driest center as well as transferring more liquid to the adjacent SAP laminated layers.

It was expected that wicking layer with "circles" bonded pattern that contained less SAP and wicked freely in both the transverse and longitudinal directions would transfer more liquid to the SAP laminate removable pieces since it was expected to better wet both of them and have the wicking distance less inhibited by absorption of SAP within the wicking layer. What happened instead was that the removable SAP laminate pieces in the longitudinal position in the Corduroy system absorbed much more liquid and combining that better transfer of liquid out of the wicking layer with the additional drying action of the SAP within the sheet, yielded the removable piece in the center with the least wetness.

From the foregoing, it will observed that numerous modifications and variations can be effected without departing without departing from the true spirit and scope of the novel concept of the present invention. It is to be understood that no limitation with respect to the specific embodiments disclosed herein in intended or should be inferred. The disclosure is intended to cover by the appended claims all such modifications which fall within the scope of the claims.

What is claimed is:

1. A layered absorbent structure, comprising:
a central wicking layer, and a first liquid storage layer positioned in a liquid-transferring relationship on a first side of said central wicking layer,
said central wicking layer comprising hydrogen-bonded cellulosic fibrous material that comprises a plurality of a cellulosic fibers bonded together by hydrogen bonds within the central wicking layer, said central wicking layer having a corduroy bonding pattern having parallel bonded lines and unbonded space between the parallel bonded lines, the parallel bonded lines having a width of approximately 1 millimeter (mm), and where an area of a surface of said central wicking layer that corresponds to the parallel bonded lines is 5% of a total area of the surface of said central wicking layer,
said first liquid storage layer comprising a matrix of adhesive filaments and absorbent particles, said adhesive filaments adhering said first liquid storage layer to said first side of said central wicking layer,
said first liquid storage layer comprising a cellulosic fiber tissue layer adhered to the matrix of adhesive filaments and absorbent particles on the side of the matrix opposite said central wicking layer.

2. A layered absorbent structure in accordance with claim 1, wherein
said central wicking layer is comprised of a hydrogen-bonded, airlaid cellulosic fibrous material bonded by applying heat and pressure.

3. A layered absorbent structure in accordance with claim 1, wherein said layered absorbent structure exhibits a Vertical Delamination Strength greater than 4N.

4. A layered absorbent structure in accordance with claim 1, further comprising a second liquid storage layer positioned in a liquid-transferring relationship on a second side of said central wicking layer, said second side opposite to said first side, said second liquid storage layer comprising a matrix of adhesive filaments and absorbent particles, said adhesive filaments adhering said second liquid storage layer to said second side of said central wicking layer, and said second liquid storage layer comprising a cellulosic fiber tissue layer adhered to the matrix of adhesive filaments and absorbent particles on the side of the matrix opposite said central wicking layer.

5. A layered absorbent structure in accordance with claim 4, wherein said first and second liquid storage layers are of equal basis weight.

6. A layered absorbent structure in accordance with claim 1, wherein
said central wicking layer comprises a central portion formed from hydrogen-bonded wood pulp fibers, and a first tissue layer and a second tissue layer that are both hydrogen-bonded to respective opposite sides of said central portion.

7. A layered absorbent structure in accordance with claim 3, wherein said central wicking layer contains up to 20% by weight of superabsorbent polymer.

8. A layered absorbent structure in accordance with claim 1, wherein said layered absorbent structure exhibits an average Gurley Stiffness of no more than 400.

9. A layered absorbent structure in accordance with claim 1, wherein said wicking layer includes bonded and unbonded regions, wherein said wicking layer presents more bonded regions in a direction transversely of said absorbent structure.

10. A layered absorbent structure, comprising:
a central wicking layer, and a first liquid storage layer positioned in a liquid-transferring relationship on a first side of said central wicking layer,
said central wicking layer comprising hydrogen-bonded cellulosic fibrous material that comprises a plurality of a cellulosic fibers bonded together by hydrogen bonds within the central wicking layer,
said first liquid storage layer comprising a matrix of adhesive filaments and absorbent particles, said adhesive filaments adhering said first liquid storage layer to said first side of said central wicking layer,
said first liquid storage layer comprising a cellulosic fiber tissue layer adhered to the matrix of adhesive filaments and absorbent particles on the side of the matrix opposite said central wicking layer;
where:
 a. the vertical delamination strength of the layered absorbent structure exceeds 4N;
 b. the central wicking layer has a corduroy bonding pattern having parallel bonded lines and unbonded space between the parallel bonded lines, the parallel bonded lines having a width of approximately 1 millimeter (mm), and an area of a surface of the central wicking layer that corresponds to the parallel bonded lines being 5% of a total area of the surface of the central wicking layer;
 c. the central wicking layer has a density in the range of 0.08 g/cc to 0.25 g/cc; and
 d. the caliper of the layered absorbent structure is 3 mm or less.

11. The layered absorbent structure in claim 10 wherein the corduroy bonding pattern suppresses wicking in the transverse direction by requiring liquid that wicks in that direction to repeatedly cross between bonded and unbonded regions while liquid wicking in the longitudinal direction does not have to traverse between bonded and unbonded regions.

12. The layered absorbent structure in claim 11 where the central wicking layer contains up to 20% by weight of superabsorbent polymer (SAP).

13. A layered absorbent structure in accordance with claim 1, where the unbonded space between the parallel bonded lines is approximately 2.9 mm.

14. A layered absorbent structure in accordance with claim 1, where the parallel bonded lines extend in a longitudinal direction, and where the corduroy bonding pattern is configured to reduce wicking in a transverse direction.

15. A layered absorbent structure in accordance with claim 1, where the central wicking layer comprises hydrogen-bonded airlaid material comprising cellulosic fibrous material and superabsorbent polymer (SAP), the hydrogen-bonded airlaid material comprising less than 20% by weight of the SAP.

16. A layered absorbent structure in accordance with claim 1, where the caliper of the layered absorbent structure is 3 mm or less.

17. A layered absorbent structure in accordance with claim 1, where said adhesive filaments comprise a pressure-sensitive, thermoplastic adhesive composition.

18. A layered absorbent structure in accordance with claim 17, where said pressure-sensitive, thermoplastic adhesive composition comprises a synthetic rubber-based pressure-sensitive adhesive.

* * * * *